United States Patent [19]
Everhart et al.

[11] Patent Number: 5,468,236
[45] Date of Patent: Nov. 21, 1995

[54] DISPOSABLE ABSORBENT PRODUCT INCORPORATING CHEMICALLY REACTIVE SUBSTANCE

[75] Inventors: Dennis Everhart, Alpharetta; Elizabeth A. Deibler, Dunwoody; Julie R. Taylor, Snellville, all of Ga.

[73] Assignee: Kimberly-Clark Corporation, Neenah, Wis.

[21] Appl. No.: 73,901

[22] Filed: Jun. 9, 1993

[51] Int. Cl.$^6$ .................................................. A61F 13/15
[52] U.S. Cl. .................................................. 604/361
[58] Field of Search .................................................. 604/361

[56] References Cited

U.S. PATENT DOCUMENTS

| Re. 29,061 | 12/1976 | Bucalo | 128/2 |
|---|---|---|---|
| 1,725,996 | 8/1929 | Peterkin | 128/270 |
| 2,844,150 | 7/1958 | Draghi | 128/285 |
| 2,905,169 | 9/1959 | Nieburgs | 128/2 |
| 3,067,743 | 12/1962 | Merton et al. | 128/270 |
| 3,067,745 | 12/1962 | Burgeni et al. | 128/285 |
| 3,172,817 | 3/1965 | Leupold et al. | 167/90 |
| 3,187,747 | 6/1965 | Burgeni et al. | 128/156 |
| 3,386,441 | 6/1968 | Merre | 128/284 |
| 3,490,454 | 11/1970 | Goldfarb et al. | 128/285 |
| 3,572,341 | 3/1971 | Glassman | 128/285 |

(List continued on next page.)

FOREIGN PATENT DOCUMENTS

| 1203760 | 4/1986 | Canada . |
|---|---|---|
| 0101981 | 3/1984 | European Pat. Off. . |
| 1935766 | 1/1971 | Germany . |
| 1082459 | 9/1967 | United Kingdom . |
| 2022423 | 12/1979 | United Kingdom . |

OTHER PUBLICATIONS

Free, A. H. and H. M. Free, "Self Testing: An Emerging Component of Clinical Chemistry", Clinical Chem., vol. 30, No. 6, 1984, pp. 829–838.

Fairley, C., et al, "Tampons: A Novel patient–Administered Method for the Assessment of Genital Human Papillomavirus Infection", The Journal of Infectious Diseases, 1992, pp. 1103–1105.

Given, Fred T. Jr., M.D., and Howard W. Jones, III, M.D. "Self–Administered Cervical Cancer Screening", *Clinical Obstetrics and Gynecology*, vol. 35, No. 1; Mar. 1992, pp. 3–12.

"Urine Collection from Disposable Diapers", *Journal Watch*, Mar. 15, 1991, p. 61.

Ahmad, T., et al, "Urine Collection from Disposable Nappies", Lancet. 1991, pp. 674–676.

(List continued on next page.)

*Primary Examiner*—Jerome L. Kruter
*Attorney, Agent, or Firm*—William E. Maycock

[57] ABSTRACT

A disposable absorbent product which includes a chemically reactive means having an end point adapted to provide a visual indication of the presence of a substance in mammalian bodily excrement, wherein the chemically reactive means is adapted to: (A) to provide the visual indication as a result of interacting with the mammalian bodily excrement; (B) the end point of the chemically reactive means is adapted to be reached within a period of time which begins with the first insult of the chemically reactive means by the substance and ends when the disposable absorbent product is discarded; and (C) the chemically reactive means is adapted to have a stable end-point, such that the visual indication remains valid within a period of time which begins when the end point is reached and ends no sooner than when the disposable absorbent product is discarded. If desired, the chemically reactive means can be adapted to provide a visual indication of the approximate concentration of the substance. The disposable absorbent product is utilized in the same manner as a product which lacks the chemically reactive means but which otherwise is functionally similar to the disposable absorbent product. Typical disposable absorbent products include tissues, wipes, and such wearable disposable absorbent products as diapers, feminine care products, incontinent care products, surgical gowns and drapes, and the like.

25 Claims, 3 Drawing Sheets

U.S. PATENT DOCUMENTS

| | | | |
|---|---|---|---|
| 3,794,024 | 2/1974 | Kokx et al. | 128/285 |
| 3,952,746 | 4/1976 | Summers | 604/361 |
| 4,022,211 | 5/1977 | Timmons et al. | 128/287 |
| 4,192,311 | 3/1980 | Felfoldi | 604/361 |
| 4,231,370 | 11/1980 | Mroz et al. | 604/361 |
| 4,266,022 | 5/1981 | Lamprecht | 435/26 |
| 4,286,596 | 9/1981 | Rubinsetin | 128/270 |
| 4,309,997 | 1/1982 | Donald | 128/270 |
| 4,318,405 | 3/1982 | Sneider | 128/263 |
| 4,351,338 | 9/1982 | Langlois et al. | 128/285 |
| 4,373,631 | 2/1983 | Friese et al. | 206/438 |
| 4,428,747 | 1/1984 | Friese et al. | 604/12 |
| 4,553,965 | 11/1985 | Conn et al. | 604/286 |
| 4,582,717 | 4/1986 | von Bittera et al. | 427/2 |
| 4,634,438 | 1/1987 | Sustmann et al. | 604/376 |
| 4,666,833 | 5/1987 | Roy et al. | 435/26 |
| 4,673,403 | 6/1987 | Lassen et al. | 604/361 X |
| 4,704,108 | 11/1987 | Okada et al. | 604/361 |
| 4,705,513 | 11/1987 | Sheldon et al. | 604/361 |
| 4,724,204 | 2/1988 | Steinbach | 435/26 |
| 4,738,674 | 4/1988 | Todd et al. | 604/361 |
| 4,754,264 | 6/1988 | Okada et al. | 604/361 X |
| 4,820,489 | 4/1989 | Rothe et al. | 422/56 |
| 4,834,733 | 5/1989 | Huntoon et al. | 604/361 |
| 4,895,567 | 1/1990 | Colo et al. | 604/361 |
| 4,971,918 | 11/1990 | Bouse et al. | 436/166 |
| 4,983,163 | 1/1991 | Winans, Jr. et al. | 604/49 |
| 5,000,749 | 3/1991 | LeVeen et al. | 604/904 |
| 5,079,174 | 1/1992 | Buck et al. | 436/538 |
| 5,084,395 | 1/1992 | Bouse et al. | 436/166 |
| 5,116,729 | 5/1992 | Ismail et al. | 435/14 |
| 5,197,958 | 3/1993 | Howell | 604/361 |
| 5,217,444 | 6/1993 | Schoenfeld | 604/361 |
| 5,266,928 | 11/1993 | Johnson | 340/604 |

OTHER PUBLICATIONS

Whitehall, J., M. A. Miller, and P. Swartzman, "Methodology for the Quantitative Culture of Urine Collected from Gel–Based Diapers", ICAAC presentation No. 1129.

"Trichomonas & Gardnerella Detection–Visual DNA probe–based assay permits simultaneous identification", Clin. Lab Prod., v. 21, N. 12.

"Biosensors Galore", Bio/Technology Vol. 10; Feb. 1992, p. 129.

"Self–Screening", JAMA, V. 231, N. 13; Mar. 31, 1975, pp. 1352–1353.

O'Malley, J. J. and J. L. Weaver, "Subinit Structure of Glucose Oxidase from Aspergillus niger", *Biochemistry*, vol. 11, No. 19; 1972, pp. 3527–3532.

Hanna, Lavelle, et al, "Antibodies to TRIC Agents in Tears and Serum of Naturally Infected Humans", *The Journal of Infectious Diseases*, vol. 127, No. 1; Jan. 1973, pp. 95–98.

Buisman, Nico J. F., et al, "Chlamydia Keratoconjunctivitis—Determination of Chlamydia trachomatis specific secretory immunoglobulin A in tears by enzyme immunoassay", Graefe's Archive for Clinical & Experimental Ophthalmology, 1992, pp. 411–415.

Chemstrip® Micra urine test strip brochure, Boehringer Mannheim Diagnostics.

Chemistrip® 10 with SG urine test strips brochure, Boehringer Mannheim Diagnostics.

Czerwinski, Anthony W. M.D., et al, "Further evaluation of the Griess test to Detect Significant Bacteriuria", *American Journal of Obstetrics and Gynecology*, vol. 110; 1971, pp. 677–681.

ELISAmate® brochure—"Enzyme Immunoassay for Detection of Antigen or Antibody on Membranes", Kirkegaard and Perry Laboratories.

Kunin, Calvin M. MD., and Jane E. DeGroot, RN, "Self–Screening for Significant Bacteriuria—Evaluation of Dip–Strip Combination Nitrite/Culture Test", JAMA, V. 231, No. 13; Mar. 31, 1975, pp. 1349–1353.

DISPOSABLE ABSORBENT PRODUCT INCORPORATING CHEMICALLY REACTIVE SUBSTANCE

BACKGROUND OF THE INVENTION

The present invention relates to a disposable absorbent product. Typical disposable absorbent products include tissues, wipes, and such wearable disposable absorbent products as diapers, feminine care products, incontinent care products, surgical gowns and drapes, and the like.

Tests conducted by medically trained personnel, e.g., physicians, nurses, medical technologists, and the like, have long been done and are well established. Although such tests have become increasingly complex and sophisticated, they also are becoming more costly. Consequently, current socioeconomic trends have given rise to a heightened interest in procedures or measurements which a person conducts on himself or herself for the purpose of acquiring information on a physiologically relevant condition, referred to hereinafter as user self-tests or USTs. Such tests frequently are carried out without consultation with a health care professional.

USTs are not new. Traditional USTs include measuring one's body weight and temperature. More contemporary procedures include blood glucose measurements, ovulation tests, and tests for the presence of human chorionic gonadotropin in urine, the basis of home pregnancy tests. More recently, the U.S. Food and Drug Administration has approved a UST for blood cholesterol. Interestingly, USTs for urinary glucose date back to the early 1900's and became more popular with the advent of insulin as a treatment for diabetes in 1922.

The use and acceptance of USTs are influenced by a variety of factors, including test simplicity, emotional aversion, medical relevance, consumer use history, and test interpretation. By way of illustration, the utility of measuring body temperature is well known and, in practice, deviations from normal body temperature often are used to determine if a medical professional needs to be consulted. Conversely, the initial use of home pregnancy tests was limited by a lack of testing experience and confidence in results, as well as by a cumbersome test format. Not until after several years of availability did these tests evolve to be user friendly and accurate, characteristics important to their market acceptance. The marketing experience for tests for in-home blood glucose monitoring, now a non-prescription (over-the-counter or OTC) UST, was similar.

The emergence of USTs as a component of clinical chemistry and, in general, health care, is to be applauded. Moreover, the number and quality of USTs are likely to increase in the future. However, USTs in general involve procedures which must be followed precisely, particularly with respect to the times for carrying out multistep procedures and determining or estimating the result. In addition, USTs typically utilize devices which have no purpose or function other than for carrying out the proscribed test.

Disposable absorbent products have been used in clinical chemistry, principally as collection devices. For example, disposable diapers have been used to collect urine samples from infants and tampons have been utilized to collect cervical cells. In addition, tampons have been used diagnostically, e.g., for the detection of increased dehydrogenases or oxidases in vaginal secretions. Such tampons, however, are used solely as clinical chemistry specimen collection devices. Their use must be supervised by a health care professional and they have many of the same limitations as USTs.

SUMMARY OF THE INVENTION

It therefore is an object of the present invention to provide a disposable absorbent product which includes a chemically reactive means.

This and other objects will be apparent to those having ordinary skill in the art from a consideration of the specification and claims which follow.

Accordingly, the present invention provides a disposable absorbent product having incorporated therein a chemically reactive means having an end point adapted to provide a visual indication of the presence of a substance in mammalian bodily excrement, wherein:

(A) the chemically reactive means is adapted to provide the visual indication as a result of interacting with the substance;

(B) the end point of the chemically reactive means is adapted to be reached within a period of time which begins with the first insult of the chemically reactive means by the substance and ends when the disposable absorbent product is discarded;

(C) the chemically reactive means is adapted to have a stable end-point, such that the visual indication remains valid within a period of time which begins when the end point is reached and ends no sooner than when the disposable absorbent product is discarded.

In certain embodiments, the disposable absorbent product may be a wearable disposable absorbent product. Such products include, by way of example only, diapers; feminine care products such as sanitary napkins, panty liners, and tampons; incontinent care products; and surgical gowns and drapes.

DETAILED DESCRIPTION OF THE INVENTION

The disposable absorbent product of the present invention has incorporated therein a chemically reactive means having an end point adapted to provide a visual indication of the presence of a substance in mammalian bodily excrement. Such product can be, for example, a tissue, wipe, or wearable disposable absorbent product.

Exemplary wearable embodiments include, by way of illustration only, diapers; feminine care products such as a sanitary napkins, panty liners, and tampons; incontinent care products; surgical gowns and drapes; and the like. Thus, the term "wearable" is used herein to mean any disposable absorbent product which is put or draped over, put on, affixed to, or inserted into a mammalian body.

As used herein, the term "mammalian bodily excrement" is meant to include any material separated and eliminated by or discharged from a mammalian body. Such material can be a solid or a fluid, and the term "fluid" means liquid or gas. Nonlimiting examples of such excrement include feces, urine, blood, menses, serum, tears, sweat, flatus, and exhalation.

The term "substance" is used herein to refer to any substance, the presence or absence of which in mammalian bodily excrement has a known relationship to an individual's health. Hence, the substance may be selected to indicate the presence or absence of a pathological disorder or to indicate or monitor an individual's physiological condition. In the latter case, it is the concentration of the substance which generally is of interest. The term "pathological disorder" is used herein to mean a disease or reaction caused by a foreign substance which elicits an immune response or disrupts a normal body function. The term "physiological condition" refers to the state of organ functions and their interrelationships which impact overall health. Accordingly, the phrase "presence of a substance in mammalian bodily excrement" is meant to encompass the presence or absence of the substance. If the substance is present, the visual indication additionally can provide information on or an estimate of the concentration of the substance. All of these variations are deemed to come within the scope of the present invention.

The term "visual indication" is used herein to mean any indication capable of being read, i.e., capable of being observed visually and understood or interpreted without the need for a special instrument or apparatus. As used herein, the term "special instrument or apparatus" means a device designed or constructed for the specific purpose of reading and/or interpreting the visual indication or an existing device inherently capable of so doing. The term does not include a device used to correct defects of vision, such as glasses and contact lenses. The term also does not include a calibration scale or color chart to relate color to substance concentration, or other instructional, informational, or interpretational aids. While a color change or the appearance or disappearance of a color are the most common forms of a visual indication, the term is not intended to be limited thereto. For example, the visual indication could be a symbol, alphanumeric character, or the like.

In chemical terms, the substance present in the mammalian bodily excrement reacts with, acts on, or is acted upon by (or is not present to react with, act on, or be acted upon by) the chemically reactive means to provide the visual indication. If present, the substance is referred to herein for the sake of simplicity as interacting with or activating the chemically reactive means. For convenience, the discharge of an amount of a substance sufficient to interact with the chemically reactive means is referred to herein as an "insult." Nonlimiting examples of substances include hydrogen ion; ion aggregate (i.e., total ion concentration); nitrite; leukocytes; glucose; ketones; blood; phenylalanine; bilirubin; urobilinogen; protein; albumin; specific enzymes, such as lactate dehydrogenase; and urine-excreted drugs. In certain embodiments of the present invention, the substance will be one of the following: hydrogen ion, ion aggregate (i.e., total ion concentration), nitrite, leukocytes, glucose, ketones, blood, phenylalanine, bilirubin, and urobilinogen.

The visual indication generally is independent of the total quantity of the substance, and, as a consequence, mammalian body excrement, to which the chemically reactive means is exposed, provided only that a sufficient quantity is present. In general, the minimum amount is simply that amount which is necessary to activate the chemically reactive means. However, the minimum amount is in part dependent upon the concentration in the mammalian bodily excrement of the specific substance of interest.

As with many analytical procedures, there generally will be a minimum or threshold level for many of the chemically reactive means which come within the scope of the present invention. That is, the amount or concentration of the substance of interest can only be detected by the chemically reactive means when such amount or concentration is above the threshold level of detection. Thus, the threshold level is the minimum amount of substance which is necessary for a given chemically reactive means and will be known or readily determined by those having ordinary skill in the art without undue experimentation.

The maximum amount of substance, on the other hand, is related to the maximum amount of mammalian bodily excrement which the disposable absorbent product was designed to absorb. Many substances of interest are excreted in relatively small quantities in comparison with the total amount of bodily excrement. Once the substance has interacted or reacted with the chemically reactive means, discharges of additional substance-containing excrement generally will have little or no effect on the visual indication provided by the chemically reactive means. Thus, the maximum amount of substance is that amount of substance contained in the total amount of bodily excrement present in the disposable absorbent product. The maximum amount of bodily excrement, in turn, is the maximum amount which the disposable absorbent product was designed to absorb.

Unlike most clinical chemistry tests and virtually all USTs, which are kinetics-based, the chemically reactive means employed in the present invention is end point-based. This perhaps is the most unique feature of the chemically reactive means. As used herein, the term "end point" means the point marking the completion of the process which provides the required visual indication. Consequently, the visual indication has not been provided until the end point of the chemically reactive means has been reached. Thus, instead of having to be read at a specific time after the chemically reactive means has interacted with the substance, the visual indication can be read over an extended period of time after the end point has been reached. This distinction over kinetics-based tests is especially significant for those disposable absorbent products where the moment of interaction of the chemically reactive means with the substance is not known.

The chemically reactive means has three characteristics. First, the chemically reactive means is adapted to provide the visual indication as a result of interacting with a substance. This means, as stated earlier, that the visual indication is capable of being visualized, i.e., capable of being read without the need for a special instrument or apparatus. It also means that there is no need to submit the disposable absorbent product or the chemically reactive means to further processing steps of any kind. For example, the disposable absorbent product does not need to be taken to a health care professional for interpretation, or submitted to a laboratory for further testing or analysis.

Second, the end point of the chemically reactive means is adapted to be reached within a period of time which begins with the first insult and ends when the disposable absorbent product is discarded. Ideally, the end point will be reached shortly after the first insult, e.g., within about 30 seconds.

Third, the chemically reactive means is adapted to have a stable end-point, such that the visual indication remains valid within a period of time which begins when the end point is reached and ends no sooner than when the disposable absorbent product is discarded. Ideally, the end point will be stable up to the time the disposable absorbent product is discarded.

It must be kept in mind that the disposable absorbent product of the present invention, notwithstanding the presence of a chemically reactive means, still functions as an absorbent product. Thus, the product is intended to absorb mammalian bodily excrement in the same manner as a product which lacks the chemically reactive means but which otherwise is functionally similar to the disposable absorbent product of the present invention. For example, if a disposable absorbent product of the present invention were a diaper, it still would function as a diaper. Because the disposable absorbent product also includes the chemically reactive means, however, the product serves two functions.

Desirably, the disposable absorbent product of the present invention is adapted to be handled after manufacture in the same manner as a product which lacks the chemically reactive means but which otherwise is functionally similar to the disposable absorbent product. That is, the presence of the chemically reactive means in the disposable absorbent product desirably does not require special packaging materials, such as light-blocking films; special packaging conditions, such as packaging under an atmosphere of nitrogen or the like; special storage and transportation, or distribution, conditions, such as refrigeration; or the like. Thus, a disposable absorbent product of the present invention ideally will be packaged, stored, shipped, and distributed, i.e., handled after manufacture, in much the same manner as related goods not containing the chemically reactive means. However, such factors as shelf life limitations, the avoidance of high storage temperatures, and compliance with government regulations may be unavoidable.

In general, the chemically reactive means can be located anywhere within the wearable disposable absorbent product where contact with a bodily excrement can occur. Desirably, the chemically reactive means will be located primarily in the portion of the product which is most likely to be exposed to a bodily excrement, i.e., an area of the product which commonly is referred to as the target zone.

Moreover, the chemically reactive means can be included in the product by any known means. By way of illustration only, the chemically reactive means can be applied by spraying, doctor blading, printing, silk-screening, and the like. Typical examples of suitable printers are direct and offset gravure printers or coaters.

The chemically reactive means can be applied to part or all of a given layer of the product. Alternatively, the chemically reactive means can be applied to or inserted in part or all of the absorbent body of the product. If desired, the chemically reactive means can be applied to a separate structure, such as a tape, sheet, or pad, which then is incorporated into the product.

Figure 1:
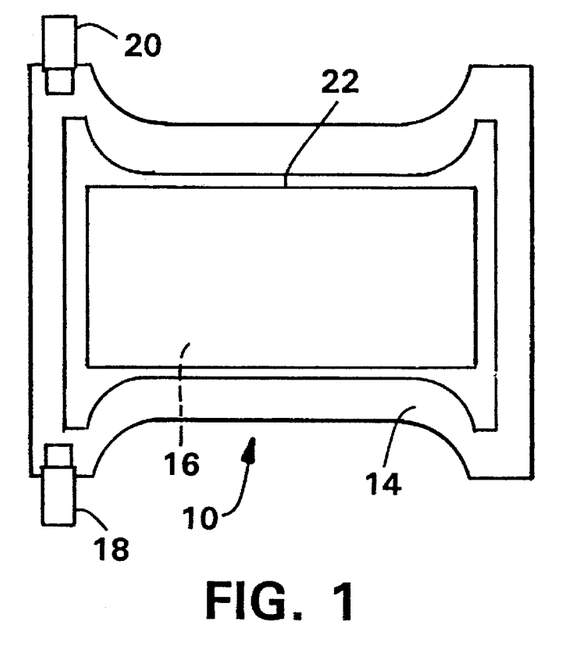
FIGS. 1–3 are plan view representations which illustrate several different embodiments of a disposable absorbent diaper of the present invention.
Figure 2:
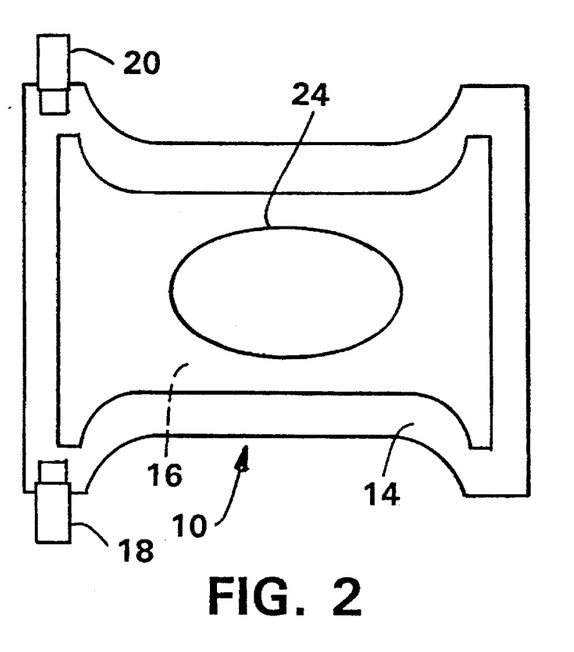
Figure 3:
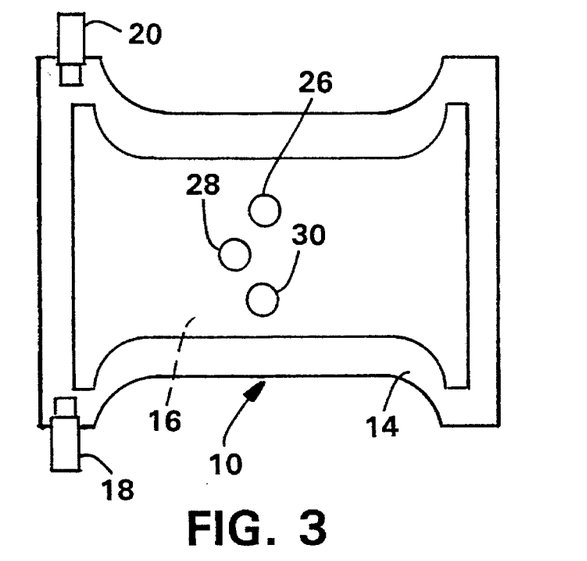

Three embodiments of a wearable disposable absorbent product, a disposable diaper, coming within the scope of the present invention are illustrated by FIGS. 1–3. Each figure is a plan view representation of the inside surface of the product (the same parts are identified with the same reference numerals in all figures). Turning first to FIG. 1, diaper 10 is formed from a liquid-impermeable backsheet or outer cover (not shown), a liquid-permeable topsheet 14 in facing superposed relation with the inner surface of the backsheet, and an absorbent body 16 which is located between the backsheet and topsheet 14. Fastening means 18 and 20 are provided to secure the diaper on the wearer. A chemically reactive means is applied to either topsheet 14 or absorbent body 16 in zone 22. FIGS. 2 and 3 are similar to FIG. 1, except for the location of the chemically reactive means. In FIG. 2, the chemically reactive means is located in zone 24. The chemically reactive means in FIG. 3 is located in zones 26, 28, and 30.

Figure 4:
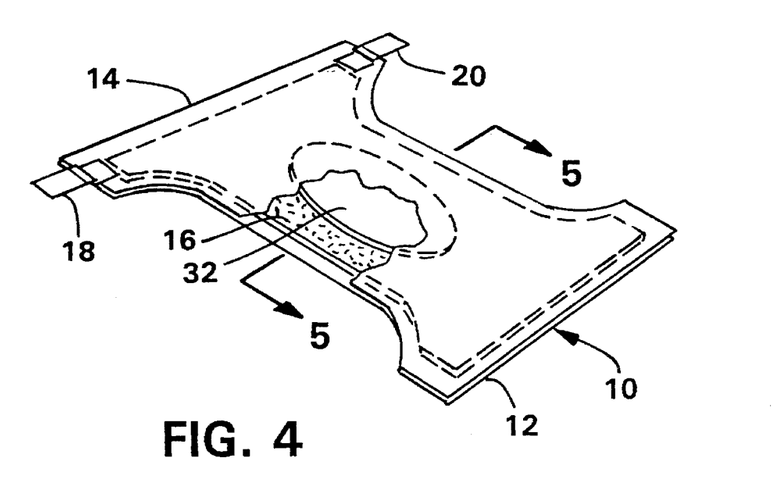
FIG. 4 is a perspective view of the inside face of a disposable diaper which illustrates another embodiment of a disposable absorbent diaper of the present invention.
Figure 5:
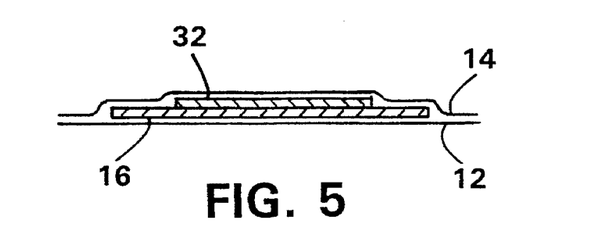
FIG. 5 is a cross-sectional view (partly schematic) taken along line 5—5 of FIG. 4.

Referring now to FIGS. 4 and 5, diaper 10 comprises a liquid-impermeable backsheet 12. An absorbent body 16 is structured and superposed on backsheet 12. Overlaying absorbent body 16 in facing superposed relation with the inner surface of backsheet 12 is a liquid-permeable topsheet 14. Fastening means 18 and 20 are provided to secure the diaper on the wearer. Situated between absorbent body 16 and topsheet 14 is oval-shaped layer 32 to which a chemically reactive means has been applied. Layer 32 can be prepared from any suitable material, such as tissue, paper, nonwoven webs, woven fabrics, and the like.

Figure 6:
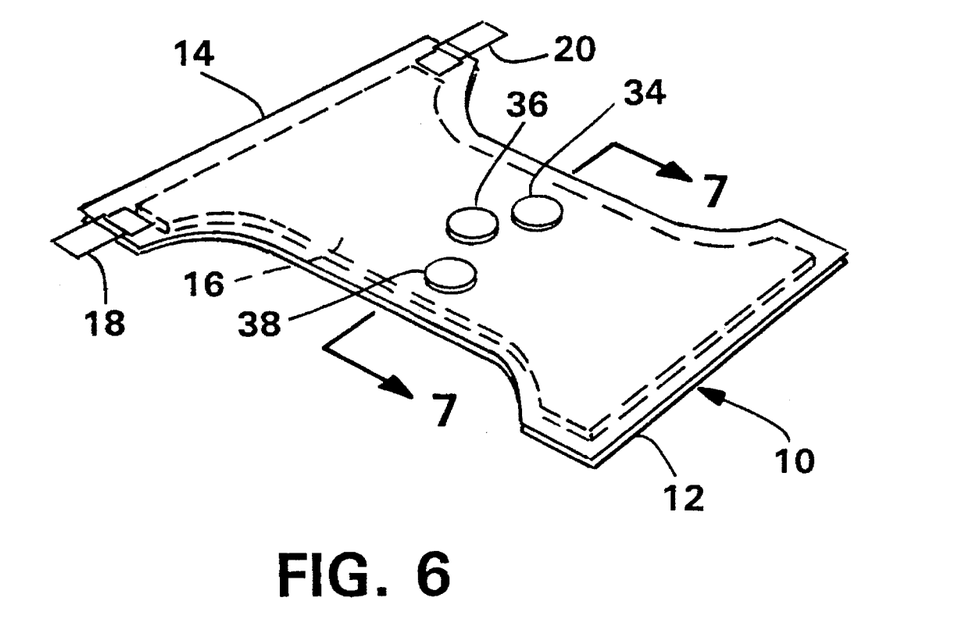
FIG. 6 is a perspective view of the inside face of a disposable diaper which illustrates still another embodiment of a disposable absorbent diaper of the present invention.
Figure 7:
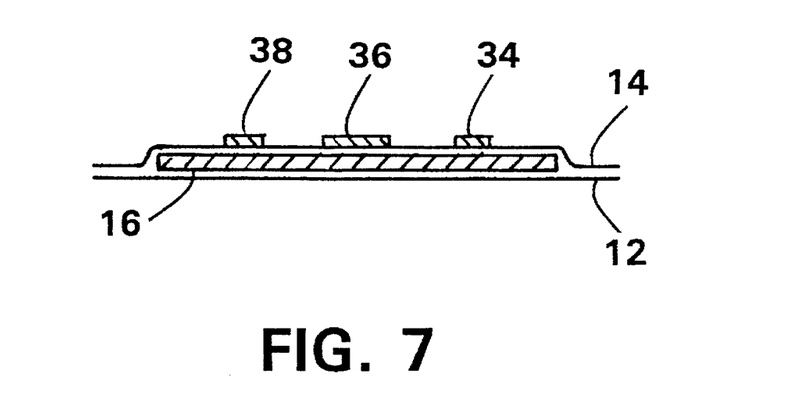
FIG. 7 is a cross-sectional view (partly schematic) taken along line 7—7 of FIG. 6.

The disposable diaper shown in FIGS. 6 and 7 is similar to that shown in FIGS. 4 and 5, except that the manner in which the chemically reactive means is incorporated into the product is different. In FIGS. 6 and 7, the chemically reactive means has been applied to layers 34, 36, and 38 which are affixed on topsheet 14 as shown. As with layer 32 of FIGS. 4 and 5, layers 34, 36, and 38 can be prepared from any suitable material. These layers can be affixed by any known means, such as by an adhesive, ultrasonic bonding, sewing, and the like.

Although the figures depict disposable absorbent diapers, it should be understood that the present invention is not limited to such a product. Moreover, the figures are not to be construed as in any way limiting either the spirit or the scope of the present invention. Thus, the present invention applies equally to disposable diapers having designs and/or a construction different from that depicted by the figures, to other wearable disposable absorbent products, and also to disposable absorbent products generally.

It will be apparent to those having ordinary skill in the art that there is a relationship among the type of disposable absorbent product to be employed, the mammalian bodily excrement, and a substance, the presence of which is to be indicated by the chemically reactive means. By way of illustration only, some examples of relationships between the type of disposable absorbent product and a particular bodily excrement are shown in Table 1.

TABLE 1

Examples of Product/Excrement Relationships

| Type of Product | Bodily Excrement |
|---|---|
| Diaper | Urine |
|  | Feces |
| Feminine Care Product | Menses |
|  | Vaginal Secretion |
| Incontinent Care Product | Urine |
|  | Feces |
| Training Pant | Urine |
|  | Feces |
| Surgical Gowns | Blood |
| Surgical Drapes | Blood |
| Facial Tissue | Sweat |

TABLE 1-continued

Examples of Product/Excrement Relationships

| Type of Product |
| --- |
| Tears |
| Mucus |

As noted above, there is a relationship between the bodily excrement and the substance. By way of illustration only, some examples of relationships between a particular bodily excrement and a specific substance are shown in Table 2.

TABLE 2

Examples of Excrement/Specific Substance Relationships

| Bodily Excrement | Specific Substance |
| --- | --- |
| Urine | Hydrogen ion |
|  | Ion aggregate |
|  | Leukocytes |
|  | Nitrite |
|  | Protein |
|  | Glucose |
|  | Ketones |
|  | Urobilinogen |
|  | Bilirubin |
|  | Red blood cells |
|  | Hemoglobin |
|  | Phenylalanine |
| Feces | Blood |
| Vaginal Secretions | Hydrogen ion |
|  | Leukocytes |
|  | Lactate dehydrogenase |
|  | *Candida albicans* |

The present invention is further described by the examples which follow. Such examples, however, are not to be construed as limiting in any way either the spirit or scope of the present invention. In the examples, all parts are by weight unless stated otherwise.

EXAMPLE 1

This example describes the preparation of a wearable disposable absorbent diaper in which the chemically reactive means is adapted to give a visual indication of urinary glucose concentration.

All reagents were obtained from commercial sources. Glucose oxidase (GOD, EC 1.1.3.4 from *Aspergillus Niger*), peroxidase (POD, EC 1.11.1.7 from Horseradish; Type VI with Rz=3.0), gelatin (type A, 300 bloom), glucose and tetramethylbenzidine (TMB) were obtained from Sigma Chemical Company, St. Louis, Mo. All glucose solutions were allowed to mutarotate for 24 hours prior to use. All other reagents were obtained from Aldrich Chemical Company, Milwaukee, Wis., and were reagent grade or better. Spectrophotometry was carried out by means of a VARIAN 2200 UV-Vis spectrophotometer. GOD was assayed following the procedure recommended by Sigma. The measured activity was 1330 GOD units/ml and the Michaelis-Menten constant at 35° C. with pH 5.0 acetate buffered solutions of glucose ranging from 0.005M to 3.0M was determined to be 0.32M. o-Dianisidine was used as the chromophore (lambda-max 500 nm) in the GOD kinetic constant determination. A molar absorptivity of 13,600 l/mole-cm for TMB was determined from a Beer's Law absorbance plot at 648 nm.

A typical glucose-indicating gel that can be applied, for example, to the absorbent core or to the topsheet of an infant diaper or adult incontinence garment is described. The composition of this gel was chosen such that a positive test for glucose would result within two minutes after the first insult, i.e., interaction with glucose, and be stable for six hours, and that the blue indicator intensity developed could differentiate between 0.1 and 10.0 mM glucose (1.8 mg/dl and 180 mg/dl). A homogeneous solution containing 10 weight-percent gelatin was prepared in pH 5.0, 50 mM citrate/phosphate buffer by mild warming. Stock solutions of known units/ml POD and GOD were prepared, both in the citrate/phosphate buffer. To 2.0 ml of the gelatin solution, 300 units of POD and 100 units of GOD were added, along with an indicated amount of TMB. This homogeneous solution could be applied to an absorbent consumer product before it would gel upon cooling to ambient temperature.

A hydrogel of gelatin was used to encapsulate GOD, POD and TMB for placement in a localized area of an infant diaper for the spot testing as illustrated in FIG. 3. Upon exposure to a synthetic urine solution containing dissolved glucose, diffusion of glucose into the gel occurs. Its enzymatic reaction with GOD produces glucolactone and the reduced state of the flavoprotein active site of GOD. This reaction is facile and occurs over the pH range of 4.0 to 9.0. In the presence of dissolved oxygen, the reduced active site of GOD is oxidized with the concomitant generation of hydrogen peroxide. This completes the GOD catalytic cycle. POD catalyzes the peroxide oxidation of TMB to produce a blue-colored complex.

The units of GOD and POD present determine the rate of peroxide and oxidized TMB production, respectively. The amount of glucose and TMB determine the intensity of the color reaction. Based on the expected range of glucose concentration to be determined, sufficient TMB, POD and GOD in the gel insures that the color intensity depends only on the glucose concentration in the test fluid. Physiological urinary glucose has an approximate concentration range from 0.0 to 30 mM (to 540 mg/dl).

The effects of TMB on the ability to differentiate glucose concentrations in the range 5 to 500 mM were examined. This is an extremely wide detection range, since 500 mM is about an order of magnitude greater than what would be considered dangerously high urinary glucose. A gel was made and deposited on a glass slide where the concentrations of GOD and POD were held constant as TMB varied. The gel consisted of the TMB plus 0.2 g gelatin, 475 units GOD, and 60 units POD, all dissolved in 4.0 ml of pH 5, 50 mM citrate/phosphate buffer. The results are summarized in Table 3.

As the results in Table 3 illustrate, different colors developed for the indicated range only when the gel contained 9.3 μmoles TMB. Lower TMB gave no differentiation, and produced only a yellow color. It was further observed that the green and blue colors which developed for the gel containing 9.3 μmoles TMB slowly turned yellow. These results indicate that under these conditions the blue color producing complex is not stable and is converted to yellow complex as the peroxide/TMB ratio increased with time. This is consistent with the failure of lower TMB concentrations to produce differentiated color within the time scale of measurement.

TABLE 3

Effects of TMB Concentration on Visual Color Developed with Glucose Indicator

| Total TMB (μmoles) | Differentiated Visible Color: Range[a] |
|---|---|
| 0.32 | No: Yellow |
| 0.62 | No: Yellow |
| 1.2 | No: Yellow |
| 9.3 | Yes: Blue/Green/Yellow |
| 4.1 | Yes: Blue/Green/Yellow[b] |

[a]Color determined 30 seconds after exposing gel to 5, 50, and 500 mM glucose.
[b]Color determined 30 seconds after exposing gel to 2.5 mM, 5.0 mM and 10 mM glucose.

A gel was made containing 4.1 μmoles of TMB which developed a blue, green or yellow color when exposed to glucose at 2.5 mM, 5.0 mM, or 10 mM, respectively. The composition of the gel consisted of 0.2 g gelatin, 100 units GOD, 300 units POD, and 6.44 μmoles (20 μg) TMB, all dissolved in 4.0 ml of pH 5.0, 50 mM acetate buffer. Upon exposing these different colored gels to 300 ppm peroxide, all became an undifferentiated yellow almost instantaneously. These results further indicate that the TMB/glucose ratio is important in being able to generate differentiated colors.

The indicator color was found to change with time, shifting from blue to yellow, and eventually turning brown. The rate of this color change with time was dependant on the TMB/glucose ratio, as illustrated in Table 4 (in the table, "NC" represents no change). Lower glucose concentrations produced a blue indicator color which persisted for longer periods of time.

The effect of peroxide concentration on UV-visible absorbance was measured. In each case, the test solution consisted of peroxide, 0.30 mM TMB, and 150 units of POD in pH 5.0, 50 mM phosphate/citrate buffer; the results are summarized in Table 5. The blue and yellow complexes are associated with absorption at 648 nm and 448 nm, respectively. Increasing concentrations of peroxide are shown to first increase absorbance at 648 nm and 365 nm, followed by reduced absorbance at these wavelengths with a concomitant appearance of intense absorbance at 448 nm. Thus, Table 5 provides insight into the color changes summarized in Tables 3 and 4.

TABLE 4

Effects of Time on Visual Color Developed

| Time After Exposure (min) | Color at Various Glucose Concentrations (mM) | | | |
|---|---|---|---|---|
| | 0 | 0.05 | 5 | 500 |
| 0 | NC | NC | NC | NC |
| 2 | NC | Lt. Blue | Blue | Dk. Blue |
| 5 | NC | Lt. Blue | Dk. Blue | Dk. Blue |
| 10 | NC | Blue | Dk. Blue | Yellow |
| 30 | NC | Green | Yellow | Brown |
| 60 | NC | Yellow | Brown | Brown |

TABLE 5

Changes in UV-Vis Absorbance with Increasing Peroxide

| Peroxide (μMoles) | Color | Absorbance (max) | | |
|---|---|---|---|---|
| | | 648 nm | 365 nm | 448 nm |
| 0 | None | — | 0.071 | — |
| 8.2 | Blue | 0.083 | 0.111 | — |
| 25 | Blue | 0.206 | 0.283 | — |
| 41 | Blue | 0.346 | 0.493 | — |
| 58 | Blue | 0.487 | 0.713 | — |
| 260 | Blue | 1.367 | 2.104 | — |
| 540 | Green | 1.242 | 2.097 | 1.16 |
| 890 | Lime | 0.261 | 0.701 | 3.66 |
| 1300 | Yellow | 0.090 | 0.382 | 4.08 |

The results discussed above allowed for the development of a urinary glucose-indicating gel which provided a stable, end point-based, visual indicator.

A gel was made containing 300 units of POD, 100 units of GOD and 3.2 μmoles of TMB. This composition was used to treat a diaper in the areas illustrated in FIG. 3. Upon exposure to synthetic urine solutions containing 0.1 and 10.0 mM glucose, a stable blue color formed with intensity readily related to the concentration of glucose. The differentiated blue intensity remained stable for three hours after which a slight yellow band began to appear around the perimeter of the gel spot. These results establish that a glucose indicating gel can be incorporated into a diaper to detect urinary glucose at concentrations which are of physiological interest.

Upon increasing the amount of TMB from 3.2 to 9.2 μmoles in the above-described gel, a stable blue color formed upon exposure to synthetic urine solutions containing 0.1 and 10.0 mM glucose, with intensity readily related to the concentration of glucose. In this case, however, the differentiated blue intensity remained stable for more than 24 hours after exposure.

EXAMPLE 2

This example is similar to Example 1, except that the specific urinary substance is nitrite. Quantofix® nitrite testing strips produced by Macherey-Nagel GmbH and Co., Duren, West Germany were obtained from Aldrich. Active pads were removed from the carrier strip and either used as received or modified with gelatin to increase time for accurate testing as described below. Synthetic urine containing known concentrations of nitrite were used as test fluids. The degree of color change was related to nitrite concentration using the vendor-provided calibration scale.

Nitrate is ubiquitous in urine, with concentrations that show a dietary dependence. Urinary tract infections (UTI) associated with bacteria containing nitrate reductases, most enteric Gram negative bacteria, are accompanied by the presence of nitrite in the urine. Consequently, the detection of urinary nitrite is usually indicative of an urinary tract infection.

The Griess test is well established for measuring bacteriuria. The principle is based on the formation of a diazonium salt by reaction of certain aromatic amines with nitrite. These in-situ formed, diazonium salts then couple with an activated aromatic compound included in the formulation to form the highly colored diazo dye. Since nitrite is not present in urine in the absence of bacteriuria, any nitrite detected is clinically significant.

Three factors are of prime importance in determining whether a positive Griess reaction will occur: (1) adequate numbers of nitrate reducing bacteria, (2) the presence of urinary nitrate, and (3) adequate incubation time of urine with nitrite producing organisms. Although 90% of UTI are associated with nitrite producing bacteria, the absence of nitrite will result in false negatives for UTI associated with most Gram positive bacteria such as Enterococci. Since nitrate is ubiquitous in urine, condition (2) is almost always satisfied. Condition three is best satisfied by testing the first urine sample voided after sleeping since a long contact time is insured.

Table 6 summarizes the results for a diaper modified with a nitrite indicator as illustrated in FIG. 3 and exposed to synthetic urine containing known amounts of nitrite. Section A of the table indicates that between 0.05 and 5.0 mg/dl of nitrite can be differentiated up to five minutes after exposure. Longer times result in lost concentration differentiation, changes in coloration, and the development of a false positive result.

To provide a format that is more suitable for a nitrite-indicating diaper and is not as sensitive to time, a gelatin coating was placed on the OTC indicator. The results for this modified indicator are summarized in Table 6, Section B. Unlike the OTC composition, concentration differentiation and maintenance of a negative control persists for the duration of the measurement, 500 seconds. These results demonstrate that a UTI-indicating function can be incorporated into an urine absorbent product to accurately measure nitrite over a time range suitable for normal consumer use.

TABLE 6

Urinary Nitrite-Indicating Diaper

| Time (min) After Exposure | Color Developed at Varying Nitrite Concentrations | | | | |
|---|---|---|---|---|---|
| | 5.0 | 0.5 | 0.05 | 0.005 | Control |
| Section A. OTC Pads Incorporated into Diaper | | | | | |
| 0 | White | White | White | White | White |
| 0.5 | Dk. Pink | Pink | Lt. Pink | White | White |
| 1 | Dk. Pink | Pink | Lt. Pink | White | White |
| 5 | Dk. Pink | Pink | Lt. Pink | Lt. Pink | Lt.Pink |
| 50 | Dk. Pink/ Pink | Pink/ Lt. Pink | Lt. Pink/ White | Lt. Pink | Lt. Pink |
| 500 | Pink | Lt. Pink | White | White | Lt. Pink |
| Section B. Gelatin-Coated Nitrite Indicator in Diaper | | | | | |
| 0 | White | White | White | White | White |
| 0.5 | Pink | Lt. Pink | White | White | White |
| 1 | Pink | Lt. Pink | White | White | White |
| 5 | Pink | Lt. Pink | White | White | White |
| 50 | Pink | Lt. Pink | White | White | White |
| 500 | Pink | Lt. Pink | White | White | White |

Having thus described the invention, numerous changes and modifications hereof will be readily apparent to those having ordinary skill in the art without departing from the spirit or scope of the invention.

What is claimed is:

1. A disposable absorbent product comprising a chemically reactive means, wherein:

said chemically reactive means has an end point adapted to provide a visual indication of the presence of a substance in mammalian bodily excrement;

said chemically reactive means is adapted to provide said visual indication as a result of interacting with said substance;

the end point of said chemically reactive means is adapted to be reached within a period of time which begins with a first insult of said chemically reactive means by said substance and ends when said disposable absorbent product is discarded;

said chemically reactive means is adapted to have a stable end-point, such that said visual indication remains valid within a period of time which begins when the end point is reached and ends no sooner than when said disposable absorbent product is discarded; and said disposable absorbent product is utilized in the same manner as a product which lacks said chemically reactive means but which otherwise is functionally similar to said disposable absorbent product.

2. The disposable absorbent product of claim 1, in which said chemically reactive means is adapted to provide a visual indication of an approximate concentration of said substance.

3. The disposable absorbent product of claim 1, in which said disposable absorbent product is adapted to be handled after manufacture in a same manner as a product which lacks said chemically reactive means but which otherwise is functionally similar to said disposable absorbent product.

4. A wearable disposable absorbent product comprising a chemically reactive means, wherein:

said chemically reactive means has an end point adapted to provide a visual indication of the presence of a substance in mammalian bodily excrement;

said chemically reactive means is adapted to provide said visual indication as a result of interacting with said substance;

the end point of said chemically reactive means is adapted to be reached within a period of time which begins with a first insult of said chemically reactive means by said substance and ends when said wearable disposable absorbent product is discarded;

said chemically reactive means is adapted to have a stable end-point, such that said visual indication remains valid within a period of time which begins when the end point is reached and ends no sooner than when said wearable disposable absorbent product is discarded; and said wearable disposable absorbent product is utilized in the same manner as a product which lacks said chemically reactive means but which otherwise is functionally similar to said wearable disposable absorbent product.

5. The disposable absorbent product of claim 4, in which said chemically reactive means is adapted to provide a visual indication of an approximate concentration of said substance.

6. The wearable disposable absorbent product of claim 4, in which said visual indication is independent of the total quantity of said substance with which said chemically reactive means interacts.

7. The wearable disposable absorbent product of claim 5, in which said wearable disposable absorbent product is adapted to be handled after manufacture in a same manner as a product which lacks said chemically reactive means but which otherwise is functionally similar to said wearable disposable absorbent product.

8. The wearable disposable absorbent product of claim 4, in which the presence of said specific substance is an indication of a pathological disorder or a physiological condition.

9. The wearable disposable absorbent product of claim 4, in which said chemically reactive means is located only in at least one predetermined area.

10. The wearable disposable absorbent product of claim 4, in which said mammalian bodily excrement is urine.

11. The wearable disposable absorbent product of claim 10, in which said product is a diaper, training pant, or an incontinent care product.

12. The wearable disposable absorbent product of claim 4, in which said mammalian bodily excrement is menses.

13. The wearable disposable absorbent product of claim 12, in which said product is a feminine care product.

14. The wearable disposable absorbent product of claim 4, in which said mammalian bodily excrement is a vaginal secretion.

15. The wearable disposable absorbent product of claim 14, in which said product is a feminine care product.

16. The wearable disposable absorbent product of claim 12, in which a specific substance is selected from the group consisting of hydrogen ion, ion aggregate, nitrite, leukocytes, glucose, ketones, blood, phenylalanine, bilirubin, and urobilinogen.

17. A disposable absorbent diaper comprising a chemically reactive means, wherein:

said chemically reactive means has an end point adapted to provide a visual indication of the presence of a substance in mammalian bodily excrement;

said chemically reactive means is adapted to provide said visual indication as a result of interacting with said substance;

the end point of said chemically reactive means is adapted to be reached within a period of time which begins with a first insult of said chemically reactive means by said substance and ends when said disposable absorbent diaper is discarded;

said chemically reactive means is adapted to have a stable end-point, such that said visual indication remains valid within a period of time which begins when the end point is reached and ends no sooner than when said disposable absorbent diaper is discarded; and said disposable absorbent diaper is utilized in the same manner as a product which lacks said chemically reactive means but which otherwise is functionally similar to said disposable absorbent diaper.

18. The disposable absorbent diaper of claim 17, in which said chemically reactive means is adapted to provide a visual indication of an approximate concentration of said substance.

19. The disposable absorbent diaper of claim 17, in which said disposable absorbent diaper is adapted to be handled after manufacture in a same manner as a product which lacks said chemically reactive means but which otherwise is functionally similar to said disposable absorbent diaper.

20. A disposable feminine care product comprising a chemically reactive means, wherein:

said chemically reactive means has an end point adapted to provide a visual indication of the presence of a substance in mammalian bodily excrement;

said chemically reactive means is adapted to provide said visual indication as a result of interacting with said substance;

the end point of said chemically reactive means is adapted to be reached within a period of time which begins with a first insult of said chemically reactive means by said substance and ends when said disposable feminine care product is discarded;

said chemically reactive means is adapted to have a stable endpoint, such that said visual indication remains valid within a period of time which begins when the end point is reached and ends no sooner than when said disposable feminine care product is discarded; and said disposable feminine care product is utilized in the same manner as a product which lacks said chemically reactive means but which otherwise is functionally similar to said disposable feminine care product.

21. The disposable feminine care product of claim 20, in which said chemically reactive means is adapted to provide a visual indication of an approximate concentration of said substance.

22. The disposable feminine care product of claim 20, in which said disposable feminine care product is adapted to be handled after manufacture in a same manner as a product which lacks said chemically reactive means but which otherwise is functionally similar to said disposable feminine care product.

23. A disposable incontinent care product comprising a chemically reactive means, wherein:

said chemically reactive means has an end point adapted to provide a visual indication of the presence of a substance in mammalian bodily excrement;

said chemically reactive means is adapted to provide said visual indication as a result of interacting with said substance;

the end point of said chemically reactive means is adapted to be reached within a period of time which begins with a first insult of said chemically reactive means by said substance and ends when said disposable incontinent care product is discarded;

said chemically reactive means is adapted to have a stable end-point, such that said visual indication remains valid within a period of time which begins when the end point is reached and ends no sooner than when said disposable incontinent care product is discarded; and said disposable incontinent care product is utilized in the same manner as a product which lacks said chemically reactive means but which otherwise is functionally similar to said disposable incontinent care product.

24. The disposable incontinent care product of claim 23, in which said chemically reactive means is adapted to provide a visual indication of an approximate concentration of said substance.

25. The disposable incontinent care product of claim 23, in which said disposable incontinent care product is handled in a same manner as a product which lacks said chemically reactive means but which otherwise is functionally similar to said disposable incontinent care product.

* * * * *